United States Patent
Faries et al.

(10) Patent No.: US 8,153,937 B2
(45) Date of Patent: *Apr. 10, 2012

(54) THERMAL TREATMENT SYSTEM INSTRUMENT RACK AND METHOD OF SELECTIVELY THERMALLY TREATING MEDICAL INSTRUMENT PORTIONS

(75) Inventors: Durward I Faries, Las Vegas, NV (US); Bruce R Heymann, Vienna, VA (US); David Hendrix, Ashburn, VA (US)

(73) Assignee: Ecolab Inc., St. Paul, MN (US)

( * ) Notice: Subject to any disclaimer, the term of this patent is extended or adjusted under 35 U.S.C. 154(b) by 98 days.

This patent is subject to a terminal disclaimer.

(21) Appl. No.: 12/763,384

(22) Filed: Apr. 20, 2010

(65) Prior Publication Data

US 2010/0200561 A1 Aug. 12, 2010

Related U.S. Application Data

(63) Continuation of application No. 11/086,656, filed on Mar. 23, 2005, now Pat. No. 7,728,262.

(60) Provisional application No. 60/555,327, filed on Mar. 23, 2004.

(51) Int. Cl.
*A61B 19/10* (2006.01)
*F27D 11/00* (2006.01)
*A61F 7/00* (2006.01)

(52) U.S. Cl. ........ 219/429; 219/430; 219/433; 219/439; 604/114

(58) Field of Classification Search .................. None
See application file for complete search history.

(56) References Cited

U.S. PATENT DOCUMENTS

| 2,174,425 | A |   | 9/1939  | Schlumbohm |
|-----------|---|---|---------|------------|
| 2,323,356 | A |   | 7/1943  | Rosay |
| 2,599,192 | A | * | 6/1952  | Miller .......................... 108/149 |
| 2,613,511 | A |   | 10/1952 | Walsh |
| 2,807,701 | A |   | 9/1957  | Conlin et al. |
| 3,685,507 | A |   | 8/1972  | Donnelly |
| 3,807,954 | A |   | 4/1974  | McDonald |
| 3,869,596 | A |   | 3/1975  | Howie |
| 3,902,484 | A |   | 9/1975  | Winters |
| 3,942,510 | A |   | 3/1976  | Garrett |
| 4,053,954 | A | * | 10/1977 | Chapman ......................... 4/559 |
| 4,270,067 | A |   | 5/1981  | Thomas et al. |
| 4,284,880 | A |   | 8/1981  | Keiser |

(Continued)

FOREIGN PATENT DOCUMENTS

JP 61-185967 11/1986

(Continued)

*Primary Examiner* — Joseph M Pelham
(74) *Attorney, Agent, or Firm* — Edell, Shapiro & Finnan LLC

(57) ABSTRACT

A system according to the present invention includes a cabinet, a basin positioned within the cabinet to contain and thermally treat a liquid bath, and a rack or tray disposed on the cabinet that supports exposed scope optics above the liquid bath within the basin. The scope optics resides outside of the bath in a dry state, thereby permitting the remaining scope portions within the bath to be thermally treated. This enables accurate temperature warming of the scope to reduce trauma of tissue and retrieval of enhanced images by the scope during a medical procedure. The present invention permits medical personnel or operating room staff to warm scopes in a controlled environment while maintaining scope optics in a dry state.

5 Claims, 1 Drawing Sheet

U.S. PATENT DOCUMENTS

| | | | |
|---|---|---|---|
| 4,393,659 A | 7/1983 | Keyes et al. | |
| 4,458,139 A | 7/1984 | McClean | |
| 4,474,016 A | 10/1984 | Winchell | |
| 4,516,564 A | 5/1985 | Koiso et al. | |
| 4,522,041 A | 6/1985 | Menzel | |
| 4,625,098 A | 11/1986 | Joe | |
| 4,782,835 A | 11/1988 | Bernardini | |
| 4,828,876 A | 5/1989 | Ohhara et al. | |
| 4,869,271 A | 9/1989 | Idris | |
| 4,903,710 A | 2/1990 | Jessamine et al. | |
| 4,934,152 A | 6/1990 | Templeton | |
| 4,967,061 A | 10/1990 | Weber, Jr. et al. | |
| 5,040,699 A | 8/1991 | Gangemi | |
| 5,042,455 A | 8/1991 | Yue et al. | |
| 5,042,981 A | 8/1991 | Gross | |
| RE33,854 E | 3/1992 | Adair | |
| 5,129,033 A | 7/1992 | Ferrara et al. | |
| 5,163,299 A | 11/1992 | Faries, Jr. et al. | |
| 5,174,306 A | 12/1992 | Marshall | |
| 5,310,524 A | 5/1994 | Campbell et al. | |
| 5,331,820 A | 7/1994 | Faries, Jr. et al. | |
| 5,333,326 A | 8/1994 | Faries, Jr. et al. | |
| 5,345,063 A | 9/1994 | Reusche et al. | |
| 5,351,675 A * | 10/1994 | Brodsky | 600/169 |
| 5,363,746 A | 11/1994 | Gordon | |
| 5,374,278 A | 12/1994 | Chesterfield et al. | |
| 5,374,813 A | 12/1994 | Shipp | |
| 5,383,476 A | 1/1995 | Peimer et al. | |
| 5,386,835 A | 2/1995 | Elphick et al. | |
| 5,396,905 A | 3/1995 | Newman | |
| 5,400,267 A | 3/1995 | Denen et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,435,322 A | 7/1995 | Marshall | |
| 5,443,082 A | 8/1995 | Mewburn | |
| 5,449,892 A | 9/1995 | Yamada | |
| 5,457,962 A | 10/1995 | Faries, Jr. et al. | |
| 5,463,213 A | 10/1995 | Honda | |
| 5,480,302 A * | 1/1996 | Fife | 433/116 |
| 5,502,980 A | 4/1996 | Faries, Jr. et al. | |
| 5,517,170 A | 5/1996 | Peters et al. | |
| 5,518,502 A | 5/1996 | Kaplan et al. | |
| 5,522,095 A | 6/1996 | Faries, Jr. et al. | |
| 5,522,805 A | 6/1996 | Vancaillie et al. | |
| 5,524,478 A | 6/1996 | Joy et al. | |
| 5,524,643 A | 6/1996 | Faries, Jr. et al. | |
| 5,531,697 A | 7/1996 | Olsen | |
| 5,539,185 A | 7/1996 | Polster | |
| 5,549,543 A * | 8/1996 | Kim | 600/169 |
| 5,551,240 A | 9/1996 | Faries, Jr. et al. | |
| 5,615,423 A | 4/1997 | Faries, Jr. et al. | |
| 5,647,840 A | 7/1997 | D'Amelio et al. | |
| 5,651,757 A | 7/1997 | Meckstroth | |
| 5,653,938 A | 8/1997 | Faries, Jr. et al. | |
| 5,658,478 A | 8/1997 | Roeschel et al. | |
| 5,664,582 A | 9/1997 | Szymaitis | |
| 5,715,547 A * | 2/1998 | Becker et al. | 4/619 |
| 5,717,188 A | 2/1998 | Vaillancourt | |
| 5,800,352 A | 9/1998 | Ferre et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,862,672 A | 1/1999 | Faries, Jr. et al. | |
| 5,879,621 A | 3/1999 | Faries, Jr. et al. | |
| 5,910,106 A | 6/1999 | Morgan et al. | |
| 5,950,438 A | 9/1999 | Faries, Jr. et al. | |
| D417,809 S * | 12/1999 | Hofman | D6/525 |
| 6,003,328 A | 12/1999 | Faries, Jr. et al. | |
| 6,035,855 A | 3/2000 | Faries, Jr. et al. | |
| 6,087,636 A * | 7/2000 | Faries et al. | 219/429 |
| 6,091,058 A | 7/2000 | Faries, Jr. et al. | |
| 6,102,044 A | 8/2000 | Naidyhorski | |
| D441,996 S * | 5/2001 | Wright | D6/525 |
| 6,231,596 B1 * | 5/2001 | Collins | 607/114 |
| 6,234,635 B1 | 5/2001 | Seitzinger et al. | |
| 6,255,627 B1 | 7/2001 | Faries, Jr. et al. | |
| 6,259,067 B1 | 7/2001 | Faries et al. | |
| D447,900 S * | 9/2001 | Wright | D6/525 |
| 6,341,704 B1 * | 1/2002 | Michel, Jr. | 211/181.1 |
| 6,371,121 B1 | 4/2002 | Faries, Jr. et al. | |
| 6,448,571 B1 | 9/2002 | Goldstein | |
| 6,586,950 B1 | 7/2003 | Sargent et al. | |
| 6,593,552 B1 | 7/2003 | Li | |
| 6,644,383 B2 | 11/2003 | Joseph et al. | |
| 6,701,174 B1 | 3/2004 | Krause et al. | |
| 6,810,881 B2 | 11/2004 | Faries, Jr. et al. | |
| 6,860,271 B2 | 3/2005 | Faries, Jr. et al. | |
| 6,884,970 B2 * | 4/2005 | Lehman | 219/432 |
| 6,910,485 B2 | 6/2005 | Faries, Jr. et al. | |
| 6,918,395 B2 | 7/2005 | Faries, Jr. et al. | |
| 6,927,365 B2 * | 8/2005 | Li | 219/432 |
| 7,041,941 B2 | 5/2006 | Faries, Jr. et al. | |
| 7,128,275 B2 | 10/2006 | Kammer et al. | |
| 7,176,030 B2 | 2/2007 | Faries, Jr. et al. | |
| 7,276,675 B2 | 10/2007 | Faries, Jr. et al. | |
| 7,307,245 B2 | 12/2007 | Faries, Jr. et al. | |
| 7,309,472 B2 * | 12/2007 | Michaelson et al. | 422/297 |
| 7,311,660 B2 | 12/2007 | Gomez | |
| 7,347,210 B2 | 3/2008 | Faries, Jr. et al. | |
| 7,350,373 B1 | 4/2008 | Faries, Jr. et al. | |
| 7,417,205 B2 | 8/2008 | Faries, Jr. et al. | |
| 7,418,966 B2 | 9/2008 | Faries, Jr. et al. | |
| 7,671,302 B1 * | 3/2010 | Faries et al. | 219/429 |
| 7,728,262 B1 | 6/2010 | Faries, Jr. et al. | |
| 7,854,230 B2 | 12/2010 | Faries, Jr. et al. | |
| 7,959,860 B2 | 6/2011 | Faries, Jr. et al. | |
| 2003/0132216 A1 | 7/2003 | Li | |
| 2003/0231990 A1 | 12/2003 | Faries, Jr. et al. | |
| 2004/0200480 A1 | 10/2004 | Faries, Jr. et al. | |
| 2004/0200483 A1 | 10/2004 | Faries, Jr. et al. | |
| 2004/0208780 A1 | 10/2004 | Faries, Jr. et al. | |
| 2005/0247169 A1 | 11/2005 | Faries, Jr. et al. | |
| 2006/0065276 A1 | 3/2006 | Kammer et al. | |
| 2006/0086361 A1 | 4/2006 | Kammer et al. | |
| 2006/0091128 A1 | 5/2006 | Kammer et al. | |
| 2006/0091129 A1 | 5/2006 | Colonna | |
| 2006/0194324 A1 | 8/2006 | Faries, Jr. et al. | |
| 2006/0260443 A1 | 11/2006 | Faries, Jr. et al. | |
| 2006/0289445 A1 | 12/2006 | Colonna | |
| 2007/0089753 A1 | 4/2007 | Faries, Jr. et al. | |
| 2009/0255540 A1 | 10/2009 | Faries, Jr. | |
| 2010/0116810 A1 | 5/2010 | Faries, Jr. et al. | |
| 2011/0270367 A1 | 11/2011 | Faries, Jr. et al. | |

FOREIGN PATENT DOCUMENTS

| | | |
|---|---|---|
| JP | 06-123532 | 5/1994 |

* cited by examiner

US 8,153,937 B2

THERMAL TREATMENT SYSTEM INSTRUMENT RACK AND METHOD OF SELECTIVELY THERMALLY TREATING MEDICAL INSTRUMENT PORTIONS

CROSS REFERENCE TO RELATED APPLICATIONS

The present application is a continuation of U.S. patent application Ser. No. 11/086,656, entitled, "Thermal Treatment System Instrument Rack and Method of Selectively Thermally Treating Medical Instrument Portions," and filed Mar. 23, 2005, which claims priority from U.S. Provisional Patent Application Ser. No. 60/555,327, entitled "Thermal Treatment System Instrument Rack and Method of Selectively Thermally Treating Medical Instrument Portions" and filed Mar. 23, 2004. The disclosures of the above mentioned patent applications are incorporated herein by reference in their entireties.

BACKGROUND OF THE INVENTION

1. Technical Field

The present invention pertains to a system for thermally treating surgical instruments. In particular, the present invention pertains to a system for warming surgical scopes in a temperature controlled liquid bath while maintaining optics of the scope in a dry state.

2. Discussion of the Related Art

Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. The surgical scopes may be warmed prior to use, where scope optics must remain dry to protect those optics and prevent distortion of the image. The scopes are warmed for several reasons, including enhancing image results and preventing infections. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections.

Currently, scopes are typically warmed in an insulated container (e.g., THERMOS) filled with warm liquid. However, since the container generally does not provide temperature control for the liquid and/or scopes, the temperature of the scope is not precisely known by medical personnel. Accordingly, medical personnel may utilize scopes at inadequate temperatures relative to a patient body, thereby potentially causing tissue trauma and fogging of the scope as described above. A chemical wipe or spray may be used to reduce fogging instead of warming the scopes; however, the chemical may be inadvertently introduced into the patient, thereby causing complications.

OBJECTS AND SUMMARY OF THE INVENTION

Accordingly, it is an object of the present invention to selectively treat portions of a surgical instrument with a temperature controlled thermal bath.

It is another object of the present invention to maintain the optics of a surgical scope disposed in a thermal treatment system basin in a dry state.

Yet another object of the present invention is to maintain the optics of a surgical scope in a dry state by supporting the optics above heated surgical liquid.

A further object of the present invention is to maintain optics of a surgical scope in a dry state by supporting the optics above heated surgical liquid within a thermal treatment system basin using a rack disposed above the basin.

According to the present invention, a system includes a cabinet, a basin positioned within the cabinet to contain and thermally treat a liquid bath, and a rack or tray disposed on the cabinet that supports exposed scope optics above the liquid bath within the basin. The scope optics resides outside of the bath in a dry state, thereby permitting the remaining scope portions within the bath to be thermally treated. This enables accurate temperature warming of the scope to reduce trauma of tissue and retrieval of enhanced images by the scope during a medical procedure. The present invention permits medical personnel or operating room staff to warm scopes in a controlled environment while maintaining scope optics in a dry state.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
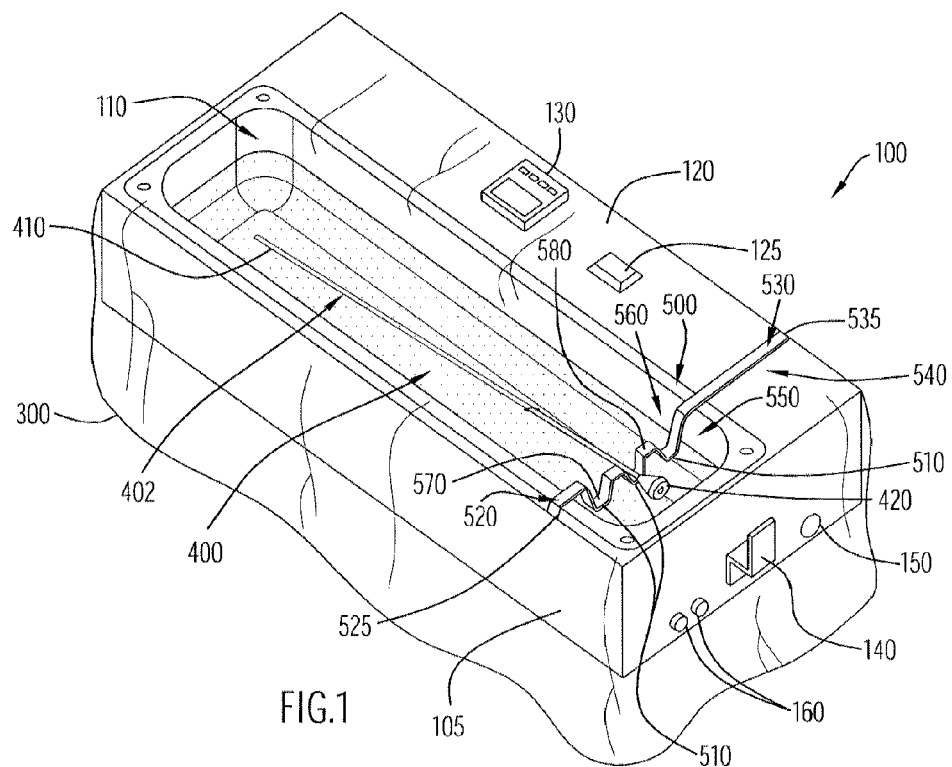
FIG. 1 is a view in perspective of an exemplary thermal treatment system employing an instrument tray or rack to selectively treat instrument portions according to the present invention.

An exemplary thermal treatment system employing an instrument tray or rack according to the present invention is illustrated in FIG. 1. Specifically, thermal treatment system 100 for thermally treating a sterile medium (e.g., solution or liquid) includes a cabinet or housing 105 in the form of a generally rectangular block and a warming basin 110 recessed into a top surface 120 of cabinet 105. Basin 110 may be of any shape; however, by way of example only, the basin is illustrated as being substantially rectangular. A heater power switch 125 and a temperature controller/indicator 130 are provided on top surface 120 adjacent the warming basin. A support hook 140 is disposed on the cabinet front wall (e.g., as viewed in FIG. 1) and may support a system power cord (not shown). Electrical connections may be made to cabinet 105 via a power port 150 disposed on the cabinet front wall adjacent hook 140. In addition, fuse receptacles 160 may be disposed on the cabinet front wall proximate hook 140 to receive fuses in order to prevent damage to circuitry (e.g., FIG. 2) contained within cabinet 105.

Figure 2:
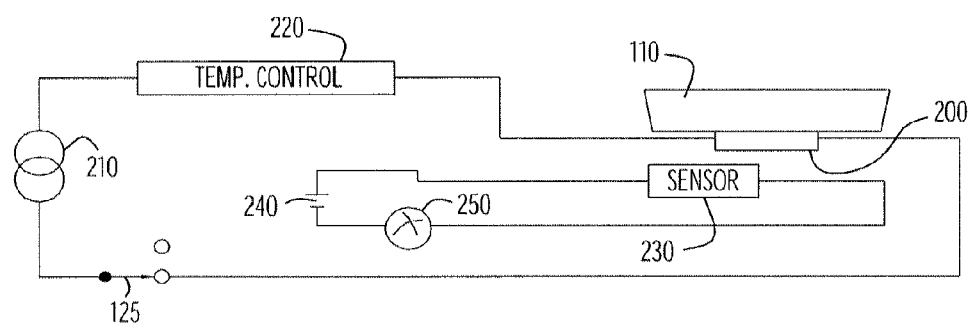
FIG. 2 is an electrical schematic diagram of the heating unit employed by the thermal treatment system of FIG. 1.

The manner of heating sterile liquid in a warming basin (e.g., warming basin 110 of FIG. 1) is illustrated schematically in FIG. 2. Specifically, an electrical circuit includes a power source 210 connected in series with a temperature control unit 220, a heater element or pad 200 and power control switch 125. Heater element 200 is typically a thin, wafer-like member disposed along the bottom surface of warming basin 110, secured to the basin by a suitable pressure sensitive adhesive having efficient heat transfer characteristics. Heater element 200 has smaller dimensions than those of the basin bottom and is disposed at the approximate center of the basin bottom surface. Heater element 200 may alternatively be of any quantity (e.g., at least one), shape or size, and may include any configuration (e.g., strips, bars, segments, etc.) that covers the entirety or any portion of the basin. In addition, the heater element may be implemented by any conventional or other type of heater or heating element (e.g., heating coils, etc.) that may be disposed on the basin at any suitable locations.

Temperature control unit 220 includes a device for adjusting current passing through heater element 200 so as to permit selective adjustment of the heat applied to basin 110 (and thus the liquid in the basin). Power switch 125 permits selective application and removal of current flow with respect to heater element 200. Heater element 200 is controlled by controller 220 in accordance with an entered desired temperature and temperatures measured by a temperature sensor 230 as described below.

Temperature sensor 230 is preferably implemented by a conventional resistive temperature device (RTD) (e.g., a 1,000 Ohm RTD). However, the sensor may be implemented by any conventional or other type of temperature sensor, and may be disposed at any suitable location on the basin or within the cabinet. By way of example only, temperature sensor 230 is disposed adjacent basin 110 to sense the temperature of the basin, the liquid contained therein, and/or the heater element. Sensor 230 is connected in series with a voltage source 240 and an indicator 250. Voltage source 240 and power source 210 may be the same source, or the voltage for one may be derived from the other. Indicator 250 measures the current through temperature sensor 230, with the current being proportional to the sensed temperature. Indicator 250 and temperature controller 220 may correspond, for example, to temperature controller/indicator 130 described above. For further examples of these types of heating units, reference is made to U.S. Pat. Nos. 5,333,326 (Faries, Jr. et al.) and 6,087,636 (Faries, Jr. et al.), the disclosures of which are incorporated herein by reference in their entireties.

It is to be understood that the thermal treatment system described above may have various configurations. For example, the thermal treatment system may be configured to cool and/or congeal the medium to produce cooled liquid or surgical slush. In this instance, the heater element may be replaced by refrigeration devices that are controlled in substantially the same manner described above. Furthermore, the thermal treatment system may include a plurality of basins warming and/or cooling a sterile medium as described above. In addition, the system may be configured to attach to a stand or another system cabinet or may be configured as a stand-alone unit. Examples of these types of system configurations are disclosed in U.S. Pat. Nos. 5,333,326 (Faries, Jr. et al.), 5,429,801 (Faries, Jr. et al.), 5,522,095 (Faries, Jr. et al.), 5,524,643 (Faries, Jr. et al.), 5,615,423 (Faries, Jr. et al.), 5,653,938 (Faries, Jr. et al.), 5,816,252 (Faries, Jr. et al.), 5,862,672 (Faries, Jr. et al.), 5,857,467 (Faries, Jr. et al.), 5,879,621 (Faries, Jr. et al.), 6,091,058 (Faries, Jr. et al.), and/or 6,255,627 (Faries, Jr. et al). The disclosures of the above-mentioned patents are incorporated herein by reference in their entireties.

Referring back to FIG. 1, a sterile drape 300, preferably transparent, is typically disposed over the top and sides of cabinet 105. Power switch 125 and controller 130 are disposed on top surface 120 of system cabinet 105 and are adjustable manually through drape 300. The portion of drape 300 disposed in basin 110 serves as a sterile container or receptacle for sterile liquid to be heated and placed therein. Typical sterile liquid treated by the thermal treatment system is a 0.80% to 0.95% sodium chloride solution (i.e., saline). Drape 300 is made from a material that is impervious to the sterile liquid and sufficiently soft and flexible to conform to basin walls. The thickness of the drape is preferably minimized to render thermal transfer therethrough most efficient, yet the thickness is sufficient to resist tearing and puncturing during normal use. The drape may be made of materials commonly used in hospitals for surgical drapes and has a thickness, by way of example only, of approximately 4.5 to 6.0 mils. However, the drape may have any desired thickness. Drape 300 may also be made of polyurethane film as disclosed for the drape in U.S. Pat. No. 4,934,152 (Templeton), the disclosure of which is incorporated herein by reference in its entirety. In addition, the drape may include sensors to detect the presence or absence of liquid within the basin and/or the presence of a drape leak. Examples of these types of drapes are disclosed in U.S. Pat. No. 6,810,881 (Faries, Jr. et al.), as well as in U.S. Patent Application Publication Nos. 2003/0172937 (Faries, Jr. et al.) and 2003/0231990 (Faries, Jr. et al.), the disclosures of which are incorporated herein by reference in their entireties.

The drape may further include a preformed container portion (not shown) contoured to match the contour of a basin. The preformed container portion is typically thicker than the remaining portions of the drape described above in order to resist puncture and enable the container portion to maintain the shape of the basin. By way of example only, the container portion may be made of a heavy gauge polyethylene/ionomer resin blend having a thickness of approximately 10 to 16 mils. The percentage of ionomer resin in the blend is in the approximate range of forty to seventy percent. The drapes described above are designed to be disposable after a single use and are provided presterilized and prepackaged in a manner to preserve its sterile state during storage.

Drape 300 is typically positioned over thermal treatment system 100 such that a portion of the drape is disposed in basin 110 to form a drape receptacle. The drape forms a sterile field above the basin to maintain sterility of a sterile medium placed in the drape receptacle. Generally, objects (e.g., medical instruments, containers, etc.) may be warmed in the basin by placing the objects in heated liquid within basin 110 (and contained by the drape receptacle).

Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. A conventional or other surgical scope 400 typically includes a shaft member 402 with a distal portion 410 for insertion into a patient body. The scope distal end typically includes a lens to capture and transmit images. The shaft member proximal end includes optics unit 420 (e.g., a lens, etc.). Fiber optics (not shown) generally extend along the interior of the shaft member to transmit image data from the scope distal end to optics unit 420 for conveyance to the surgeon (e.g., via an eyepiece, camera or other device that may be coupled to the optics unit).

Surgical scopes may be warmed prior to use, where scope optics must remain dry to protect those optics and prevent distortion of the image. Currently, scopes are typically warmed in an insulated container (e.g., THERMOS) filled with warm liquid (e.g., without temperature control). The scopes are warmed for several reasons, including enhancing image results and preventing infections. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. A chemical wipe or spray may alternatively be used to reduce fogging; however, the chemical may be inadvertently introduced into the patient, thereby causing complications.

Accordingly, the present invention enables medical personnel (e.g., operating room staff, etc.) to warm scopes in a controlled environment (e.g., liquid bath) while maintaining the scope optics in a dry state. In particular, system 100 may include a tray or rack 500 positioned to elevate optics unit 420 above the temperature-controlled liquid bath contained in basin 110, where the distal portions of shaft member 402 remain within the liquid for thermal treatment.

Rack 500 includes a bar 540 with a first end portion 520, a second end portion 530 and a serpentine intermediate portion 550 that includes at least one receptacle 510 operable to receive a corresponding surgical scope 400. Rack 500 may be of any shape or size, and may include any number of receptacles 510. Similarly, bar 540 may be of any size, shape, or thickness, and may include any suitable cross-sectional shape. By way of example only, the bar may be a substantially flat bar with a substantially rectangular cross section. Receptacles 510 may each be of any shape suitable to secure a corresponding scope 400 therein, while elevating optics unit 420 of the scope above the liquid bath contained within the basin. By way of further example, the intermediate portion 550 may include a series of serpentine or undulate portions 560 that form the receptacles 510. The undulate portions are basically formed by a series of alternating recesses 570 and peaks 580. The recesses form the receptacles 510, supporting the optics units of the corresponding scopes. Receptacles 510 may include dimensions slightly larger than those of shaft member 402, but smaller than those of optics unit 420. This configuration enables scope 400 to be readily placed into and removed from receptacle 510 (and thus the thermal bath), while optics unit 420 serves as a stop to prevent the scope from sliding into liquid filled basin 110. The rack may be constructed of high-density polyethylene, ABS thermoplastic, metals or steel, propylene material, or any material that is capable of withstanding temperatures typically used in thermal treatment systems (e.g., at least about 160° F.) and is sufficiently rigid to hold objects placed thereon.

As shown in FIG. 1, rack 500 extends along the shorter dimension of the generally rectangular top surface 120 of the cabinet 105. Rack peaks 580 are generally level with the top surface 120 of cabinet 105, with receptacles 510 extending below the rim of the basin. The recesses may alternatively be configured to extend above the rim of the basin (and thus above the cabinet top surface). First end portion 520 and second end portion 530 may be permanently or removably attached to the cabinet. First end portion 520 and second end portion 530 preferably include a generally U-shaped hook or engagement member 525 and 535, respectively, configured to engage corresponding portions of cabinet 105 located adjacent opposing larger dimensioned sides of basin 110. The engagement members 525, 535 stably support the rack on the system cabinet 105 to position the receptacles above the fluid line of the thermal bath. In other words, rack 500 basically rests on the cabinet portions and/or basin lips or ledges and maintains receptacles 510 above the liquid bath in the basin.

In operation, the portion of shaft member 402 immediately distal of the optics unit is placed in receptacle 510 to support the optics unit above the liquid bath. The shaft member distal portion 410 extends from the receptacle into the liquid bath for thermal treatment. Thus, the optics unit rests on the rack in a dry state, while the scope shaft member is primarily placed into the liquid bath. This allows for accurate temperature warming of selected portions of the scope, which, in turn, reduces tissue trauma and enables the scope optics unit to remain dry for clear viewing of images.

The position of rack 500 is not particularly limited. By way of example, and as shown in FIG. 1, the rack may be positioned near the front end of basin 110. However, rack 500 may be positioned at any point along the cabinet and/or basin suitable to submerge distal portions of shaft member 402 into the liquid bath, while receptacle 510 elevates optics unit 420 above the bath to maintain the optics unit in a dry state.

Operation of the system is now more fully described with reference to FIG. 1. Specifically, drape 300 is disposed over cabinet 105 and within basin 110 to form a drape receptacle as described above. Rack 500 may be disposed on cabinet 105 near the front end of basin 110. The rack may be disposed above or below drape 300 to engage scopes placed within the basin. When rack 500 is disposed below drape 300, a portion of the drape may be pushed down into each receptacle 510. Basin 110 is filled with a sterile liquid and a scope 400 is positioned in a corresponding receptacle 510, with distal portion 410 of the scope being submerged in the liquid bath and scope optics unit 420 being elevated above the bath and/or above the basin as described above. The bath may then be heated to the desired temperature via manipulation of controller 130. Alternatively, the bath may be heated before scope 400 is positioned in rack 500. Scope 400 absorbs the proper amount of thermal energy from the liquid bath in basin 110, while the optics unit of the scope remains dry, thereby preventing image distortion caused by liquid contacting exposed optics.

Rack 500 may be a separate unit as described above, or alternatively, may be formed integral with drape 300. In this case, the rack may be attached to the drape by use of ultrasonic energy, heat welding, solvents, adhesives, RF welding techniques or any other appropriate or conventional attachment process. Rack 500 may be formed on drape 300 such that the rack corresponds to, and indicates, the approximate edges of basin 110 for proper placement of the drape on the thermal treatment system. Drape 300 is disposed on cabinet 105 such that portions of the drape are pushed down into, and conform to, basin 110 to form a drape receptacle, with rack 500 positioned within the basin above the basin floor. Remaining portions of drape 300 cover top surface 120 and hang down the sides of cabinet 105. The drape receptacle typically contains a heated liquid bath, while rack 500 receives and supports scope 400 with optics unit 420 elevated above the liquid bath as described above.

It will be appreciated that the embodiments described above and illustrated in the drawings represent only a few of the many ways of implementing a thermal treatment system instrument rack and method of selectively thermally treating medical instrument portions.

The warming, cooling, and plural basin systems and their corresponding cabinets, assemblies or housings may be of any shape or size and may be constructed of any suitable materials. The plural basin system may include any quantity of heating and/or cooling basins in any combinations. The basins of the systems may be of any shape or size, may be constructed of any suitable thermal conducting materials (e.g., stainless steel, etc.) and may be disposed at any suitable locations on or within the housings. The systems may include any conventional or other heating and/or refrigeration units to thermally treat any type of sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.-160° F.). The heater element may be of any quantity (e.g., at least one), shape or size, and may include any configuration (e.g., strips, bars, segments, etc.) that covers the entirety or any portion of a basin. The heater element may be attached to a basin via any conventional or other fastening techniques (e.g., any type of adhesives, brackets, etc.). In addition, the heater element may be implemented by any conventional or other type of heater or heating element (e.g., heating coils, etc.) that may be disposed on or proximate a basin at any suitable locations.

A cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor may be implemented by any conventional or other temperature sensing device (e.g., infrared, RTD, etc.) and may be disposed at any location on or proximate a basin or within the systems. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The drapes employed with the heating, cooling and plural basin systems may be of any size or shape, and may be constructed of any suitable materials. The drapes are preferably transparent or translucent to facilitate manipulation of controls through the drape; however, these drapes may have any degree of transparency (e.g., including opaque). The drapes may be manipulated in any fashion with any portions of the drapes serving as a drape receptacle within a corresponding basin. The drapes may be of sufficient size to accommodate and form drape receptacles within any quantity of thermal treatment system basins. The drape may facilitate placement of any types of objects (e.g., instruments, containers, etc.) within the basin.

The rack may be of any quantity, size or shape, may be disposed on any part of the drape or cabinet and may be constructed of any suitable materials. The rack may be a separate unit or formed integral with and/or attached to the drape and/or preformed container portion via ultrasonic energy, heat welding, solvents, adhesives, RF welding techniques or any other attachment process. The rack may be any device capable of elevating objects above the basin floor and may be disposed in the basins above or below the drape. The rack may include any quantity of receptacles each to accommodate any quantity or portions of scopes or other objects. The rack may include any configuration (e.g., serpentine, rings, linear, dividers, etc.) to form receptacles of any quantity, shape or size to receive any medical or other objects. The basin may include any quantity of racks disposed at any locations to elevate and/or submerge any portions of medical or other items. The rack may include any quantity of any types of engagement mechanisms (e.g., clamps, brackets, hook and loop fasteners, adhesives, etc.) of any shape or size and disposed at any locations to engage the basin and/or cabinet. The rack may be configured to accommodate any quantity of basins. For example, the rack may be configured for placement in and to accommodate scopes within two or more adjacent basins.

The control circuit, power port, fuse holders, and/or other components may be disposed within the systems at any suitable locations and may be implemented by any conventional or other circuitry components arranged in any desired fashion to perform the described functions. The temperature controller may be implemented by any conventional or other temperature controller and include any desired devices for entering a temperature (e.g., buttons, keypad, etc.). The basin power switch of the systems may be implemented by any conventional or other switching device, while the fuses may be implemented by any conventional fuse or other limiting device and may be configured for any current or voltage levels. The power cord may be implemented by any conventional or other cord or cable and be configured to accommodate any desired power signals. The system may utilize any type of power source (e.g., batteries, wall outlet jack, AC, DC, etc.).

It is to be understood that the terms "top", "bottom", "front", "rear", "side", "height", "length", "width", "upper", "lower", "vertical" and the like are used herein merely to describe points of reference and do not limit the present invention to any particular orientation or configuration.

The present invention rack and/or thermal treatment systems are not limited to the applications described herein, but may be utilized for any types of medical or other items to selectively thermally treat any portions of those items.

From the foregoing description, it will be appreciated that the invention makes available a novel thermal treatment system instrument rack and method of selectively thermally treating medical instrument portions, wherein a system warms surgical scopes in a temperature controlled liquid bath while maintaining optics of the scope in a dry state.

Having described preferred embodiments of a new and improved thermal treatment system instrument rack and method of selectively thermally treating medical instrument portions, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In a thermal treatment system including a housing with a top surface and a basin recessed within said housing top surface to contain and thermally treat a sterile medium, a rack for supporting objects in the form of medical instruments within said basin comprising:

an elongated bar member including:
      a first end portion configured to engage said housing;
      a second end portion configured to engage said housing; and
      an intermediate portion between said first and second end portions and including a plurality of serpentine sections defined within said intermediate portion of said elongated bar member, wherein each serpentine section includes a recess to form a corresponding receptacle supported by said bar member above a basin floor and within an upper portion of said basin, and wherein each receptacle is configured to removably engage and elevate a portion of a corresponding object above the basin floor and said sterile medium to maintain the elevated portion in a dry state.

2. The rack of claim 1, wherein each of said end portions includes a generally U-shaped engagement member configured to engage said housing top surface.

3. The rack of claim 1, wherein said intermediate portion includes a series of alternating peaks and recesses to form said serpentine sections.

4. The rack of claim 1, wherein at least one object includes a scope with a shaft and an optics unit.

5. The rack of claim 4, wherein a receptacle of said intermediate portion includes dimensions greater than said shaft and less than said optics unit to receive said shaft and secure said scope within that receptacle.

* * * * *